(12) United States Patent
Beasley et al.

(10) Patent No.: US 11,253,640 B2
(45) Date of Patent: Feb. 22, 2022

(54) FLUID MANAGEMENT APPARATUS AND METHOD

(71) Applicant: KCI Licensing, Inc., San Antonio, TX (US)

(72) Inventors: Michael Bernard Beasley, Wimborne (GB); James Killingworth Seddon, Wimborne (GB); Christopher Brian Locke, Bournemouth (GB)

(73) Assignee: KCI Licensing, Inc., San Antonio, TX (US)

( * ) Notice: Subject to any disclaimer, the term of this patent is extended or adjusted under 35 U.S.C. 154(b) by 799 days.

(21) Appl. No.: 15/766,320

(22) PCT Filed: Nov. 17, 2016

(86) PCT No.: PCT/US2016/062555
§ 371 (c)(1),
(2) Date: Apr. 5, 2018

(87) PCT Pub. No.: WO2017/087687
PCT Pub. Date: May 26, 2017

(65) Prior Publication Data
US 2018/0289870 A1    Oct. 11, 2018

Related U.S. Application Data

(60) Provisional application No. 62/257,292, filed on Nov. 19, 2015.

(51) Int. Cl.
*A61M 1/00* (2006.01)
*H01H 35/34* (2006.01)
(Continued)

(52) U.S. Cl.
CPC .............. *A61M 1/90* (2021.05); *A61M 1/732* (2021.05); *H01H 35/346* (2013.01);
(Continued)

(58) Field of Classification Search
CPC  A61M 1/0088; A61M 1/0027; H01H 35/346; H01H 35/38
(Continued)

(56) References Cited

U.S. PATENT DOCUMENTS 1,355,846 A    10/1920  Rannells
2,547,758 A     4/1951  Keeling
(Continued)

FOREIGN PATENT DOCUMENTS

AU    550575 B2    3/1986
AU    745271 B2    3/2002
(Continued)

OTHER PUBLICATIONS

Louis C. Argenta, MD and Michael J. Morykwas, PHD; Vacuum-Assisted Closure: A New Method for Wound Control and Treatment: Clinical Experience; Annals of Plastic Surgery; vol. 38, No. 6, Jun. 1997; pp. 563-576.
(Continued)

*Primary Examiner* — Andrew J Mensh

(57) ABSTRACT

In one example embodiment, a vibration apparatus can augment and enhance negative-pressure therapy systems. The apparatus can be attached to an external surface of a dressing, fluid conductor, or other components. The apparatus can generate low-amplitude vibrations, which can be transmitted through the components. Kinetic energy of the oscillations can agitate fluid in the components, which can lower the viscosity of the fluid and reduce the frequency of blockages in fluid conductors. Vibrations may also agitate a tissue site, which can encourage blood flow and granulation.

14 Claims, 8 Drawing Sheets

(51) Int. Cl.
  *H01H 35/38* (2006.01)
  *H01H 35/26* (2006.01)
(52) U.S. Cl.
  CPC ............... *H01H 35/38* (2013.01); *A61M 1/73* (2021.05); *A61M 1/74* (2021.05); *A61M 2205/3331* (2013.01); *A61M 2205/3337* (2013.01); *H01H 35/2614* (2013.01)
(58) Field of Classification Search
  USPC ........................................................ 604/313
  See application file for complete search history.

(56) References Cited

U.S. PATENT DOCUMENTS

| | | |
|---|---|---|
| 2,632,443 A | 3/1953 | Lesher |
| 2,682,873 A | 7/1954 | Evans et al. |
| 2,910,763 A | 11/1959 | Lauterbach |
| 2,969,057 A | 1/1961 | Simmons |
| 3,066,672 A | 12/1962 | Crosby, Jr. et al. |
| 3,367,332 A | 2/1968 | Groves |
| 3,520,300 A | 7/1970 | Flower, Jr. |
| 3,568,675 A | 3/1971 | Harvey |
| 3,648,692 A | 3/1972 | Wheeler |
| 3,682,180 A | 8/1972 | McFarlane |
| 3,826,254 A | 7/1974 | Mellor |
| 4,080,970 A | 3/1978 | Miller |
| 4,096,853 A | 6/1978 | Weigand |
| 4,139,004 A | 2/1979 | Gonzalez, Jr. |
| 4,165,748 A | 8/1979 | Johnson |
| 4,184,510 A | 1/1980 | Murry et al. |
| 4,233,969 A | 11/1980 | Lock et al. |
| 4,245,630 A | 1/1981 | Lloyd et al. |
| 4,256,109 A | 3/1981 | Nichols |
| 4,261,363 A | 4/1981 | Russo |
| 4,275,721 A | 6/1981 | Olson |
| 4,284,079 A | 8/1981 | Adair |
| 4,297,995 A | 11/1981 | Golub |
| 4,333,468 A | 6/1982 | Geist |
| 4,373,519 A | 2/1983 | Errede et al. |
| 4,382,441 A | 5/1983 | Svedman |
| 4,392,853 A | 7/1983 | Muto |
| 4,392,858 A | 7/1983 | George et al. |
| 4,419,097 A | 12/1983 | Rowland |
| 4,465,485 A | 8/1984 | Kashmer et al. |
| 4,475,909 A | 10/1984 | Eisenberg |
| 4,480,638 A | 11/1984 | Schmid |
| 4,525,166 A | 6/1985 | Leclerc |
| 4,525,374 A | 6/1985 | Vaillancourt |
| 4,540,412 A | 9/1985 | Van Overloop |
| 4,543,100 A | 9/1985 | Brodsky |
| 4,548,202 A | 10/1985 | Duncan |
| 4,551,139 A | 11/1985 | Plaas et al. |
| 4,569,348 A | 2/1986 | Hasslinger |
| 4,605,399 A | 8/1986 | Weston et al. |
| 4,608,041 A | 8/1986 | Nielsen |
| 4,640,688 A | 2/1987 | Hauser |
| 4,655,754 A | 4/1987 | Richmond et al. |
| 4,664,662 A | 5/1987 | Webster |
| 4,710,165 A | 12/1987 | McNeil et al. |
| 4,733,659 A | 3/1988 | Edenbaum et al. |
| 4,743,232 A | 5/1988 | Kruger |
| 4,758,220 A | 7/1988 | Sundblom et al. |
| 4,787,888 A | 11/1988 | Fox |
| 4,826,494 A | 5/1989 | Richmond et al. |
| 4,838,883 A | 6/1989 | Matsuura |
| 4,840,187 A | 6/1989 | Brazier |
| 4,863,449 A | 9/1989 | Therriault et al. |
| 4,872,450 A | 10/1989 | Austad |
| 4,878,901 A | 11/1989 | Sachse |
| 4,897,081 A | 1/1990 | Poirier et al. |
| 4,906,233 A | 3/1990 | Moriuchi et al. |
| 4,906,240 A | 3/1990 | Reed et al. |
| 4,919,654 A | 4/1990 | Kalt |
| 4,941,882 A | 7/1990 | Ward et al. |
| 4,953,565 A | 9/1990 | Tachibana et al. |
| 4,969,880 A | 11/1990 | Zamierowski |
| 4,985,019 A | 1/1991 | Michelson |
| 5,037,397 A | 8/1991 | Kalt et al. |
| 5,086,170 A | 2/1992 | Luheshi et al. |
| 5,092,858 A | 3/1992 | Benson et al. |
| 5,100,396 A | 3/1992 | Zamierowski |
| 5,134,994 A | 8/1992 | Say |
| 5,149,331 A | 9/1992 | Ferdman et al. |
| 5,167,613 A | 12/1992 | Karami et al. |
| 5,176,663 A | 1/1993 | Svedman et al. |
| 5,215,522 A | 6/1993 | Page et al. |
| 5,232,453 A | 8/1993 | Plass et al. |
| 5,261,893 A | 11/1993 | Zamierowski |
| 5,278,100 A | 1/1994 | Doan et al. |
| 5,279,550 A | 1/1994 | Habib et al. |
| 5,298,015 A | 3/1994 | Komatsuzaki et al. |
| 5,342,376 A | 8/1994 | Ruff |
| 5,344,415 A | 9/1994 | DeBusk et al. |
| 5,358,494 A | 10/1994 | Svedman |
| 5,437,622 A | 8/1995 | Carion |
| 5,437,651 A | 8/1995 | Todd et al. |
| 5,527,293 A | 6/1996 | Zamierowski |
| 5,549,584 A | 8/1996 | Gross |
| 5,556,375 A | 9/1996 | Ewall |
| 5,607,388 A | 3/1997 | Ewall |
| 5,636,643 A | 6/1997 | Argenta et al. |
| 5,645,081 A | 7/1997 | Argenta et al. |
| 6,071,267 A | 6/2000 | Zamierowski |
| 6,135,116 A | 10/2000 | Vogel et al. |
| 6,241,747 B1 | 6/2001 | Ruff |
| 6,287,316 B1 | 9/2001 | Agarwal et al. |
| 6,345,623 B1 | 2/2002 | Heaton et al. |
| 6,488,643 B1 | 12/2002 | Tumey et al. |
| 6,493,568 B1 | 12/2002 | Bell et al. |
| 6,553,998 B2 | 4/2003 | Heaton et al. |
| 6,814,079 B2 | 11/2004 | Heaton et al. |
| 7,569,742 B2* | 8/2009 | Haggstrom ......... A61F 13/0203 602/53 |
| 7,846,141 B2 | 12/2010 | Weston |
| 8,062,273 B2 | 11/2011 | Weston |
| 8,216,198 B2 | 7/2012 | Heagle et al. |
| 8,251,979 B2 | 8/2012 | Malhi |
| 8,257,327 B2 | 9/2012 | Blott et al. |
| 8,398,614 B2 | 3/2013 | Blott et al. |
| 8,449,509 B2 | 5/2013 | Weston |
| 8,529,548 B2 | 9/2013 | Blott et al. |
| 8,535,296 B2 | 9/2013 | Blott et al. |
| 8,551,060 B2 | 10/2013 | Schuessler et al. |
| 8,568,386 B2 | 10/2013 | Malhi |
| 8,679,081 B2 | 3/2014 | Heagle et al. |
| 8,834,451 B2 | 9/2014 | Blott et al. |
| 8,926,592 B2 | 1/2015 | Blott et al. |
| 9,017,302 B2 | 4/2015 | Vitaris et al. |
| 9,198,801 B2 | 12/2015 | Weston |
| 9,211,365 B2 | 12/2015 | Weston |
| 9,289,542 B2 | 3/2016 | Blott et al. |
| 2002/0077661 A1 | 6/2002 | Saadat |
| 2002/0115951 A1 | 8/2002 | Norstrem et al. |
| 2002/0120185 A1 | 8/2002 | Johnson |
| 2002/0143286 A1 | 10/2002 | Tumey |
| 2010/0010477 A1* | 1/2010 | Augustine ........... A61M 1/0031 604/543 |
| 2012/0059294 A1* | 3/2012 | Schubert ................ A61P 17/14 601/46 |
| 2013/0338613 A1* | 12/2013 | Haggstrom ........... A61M 39/24 604/315 |
| 2014/0066868 A1* | 3/2014 | Freedman ........... A61F 13/0279 604/319 |
| 2014/0163491 A1 | 6/2014 | Schuessler et al. |
| 2015/0080788 A1 | 3/2015 | Blott et al. |

FOREIGN PATENT DOCUMENTS

| | | |
|---|---|---|
| AU | 755496 B2 | 12/2002 |
| CA | 2005436 A1 | 6/1990 |
| DE | 26 40 413 A1 | 3/1978 |
| DE | 43 06 478 A1 | 9/1994 |

(56) References Cited

FOREIGN PATENT DOCUMENTS

| | | |
|---|---|---|
| DE | 29 504 378 U1 | 9/1995 |
| EP | 0100148 A1 | 2/1984 |
| EP | 0117632 A2 | 9/1984 |
| EP | 0161865 A2 | 11/1985 |
| EP | 0358302 A2 | 3/1990 |
| EP | 1018967 A1 | 7/2000 |
| FR | 1543645 A | 10/1968 |
| GB | 692578 A | 6/1953 |
| GB | 1204132 A | 9/1970 |
| GB | 2004942 A | 4/1979 |
| GB | 2 195 255 A | 4/1988 |
| GB | 2 197 789 A | 6/1988 |
| GB | 2 220 357 A | 1/1990 |
| GB | 2 235 877 A | 3/1991 |
| GB | 2 329 127 A | 3/1999 |
| GB | 2 333 965 A | 8/1999 |
| JP | 4129536 B2 | 8/2008 |
| SG | 71559 | 4/2002 |
| WO | 80/02182 A1 | 10/1980 |
| WO | 87/04626 A1 | 8/1987 |
| WO | 90/010424 A1 | 9/1990 |
| WO | 93/009727 A1 | 5/1993 |
| WO | 94/020041 A1 | 9/1994 |
| WO | 96/05873 A1 | 2/1996 |
| WO | 97/18007 A1 | 5/1997 |
| WO | 99/13793 A1 | 3/1999 |
| WO | 2005105175 A1 | 11/2005 |
| WO | 2007030601 A2 | 3/2007 |
| WO | 2010093753 A1 | 8/2010 |

OTHER PUBLICATIONS

Susan Mendez-Eatmen, RN; "When wounds Won't Heal" RN Jan. 1998, vol. 61 (1); Medical Economics Company, Inc., Montvale, NJ, USA; pp. 20-24.
James H. Blackburn II, MD et al.: Negative-Pressure Dressings as a Bolster for Skin Grafts; Annals of Plastic Surgery, vol. 40, No. 5, May 1998, pp. 453-457; Lippincott Williams & Wilkins, Inc., Philidelphia, PA, USA.
John Masters; "Reliable, Inexpensive and Simple Suction Dressings"; Letter to the Editor, British Journal of Plastic Surgery, 1998, vol. 51 (3), p. 267; Elsevier Science/The British Association of Plastic Surgeons, UK.
S.E. Greer, et al. "The Use of Subatmospheric Pressure Dressing Therapy to Close Lymphocutaneous Fistulas of the Groin" British Journal of Plastic Surgery (2000), 53, pp. 484-487.
George V. Letsou, MD., et al.; "Stimulation of Adenylate Cyclase Activity in Cultured Endothelial Cells Subjected to Cyclic Stretch"; Journal of Cardiovascular Surgery, 31, 1990, pp. 634-639.
Orringer, Jay, et al; "Management of Wounds in Patients with Complex Enterocutaneous Fistulas"; Surgery, Gynecology & Obstetrics, Jul. 1987, vol. 165, pp. 79-80.
International Search Report for PCT International Application PCT/GB95/01983; dated Nov. 23, 1995.
PCT International Search Report for PCT International Application PCT/GB98/02713; dated Jan. 8, 1999.
PCT Written Opinion; PCT International Application PCT/GB98/02713; dated Jun. 8, 1999.
PCT International Examination and Search Report, PCT International Application PCT/GB96/02802; dated Jan. 15, 1998 & Apr. 29, 1997.
PCT Written Opinion, PCT International Application PCT/GB96/02802; dated Sep. 3, 1997.
Dattilo, Philip P., Jr., et al.; "Medical Textiles: Application of an Absorbable Barbed Bi-directional Surgical Suture" Journal of Textile and Apparel, Technology and Management, vol. 2, Issue 2, Spring 2002, pp. 1-5.
Kostyuchenok, B.M., et al.; "Vacuum Treatment in the Surgical Management of Purulent Wounds"; Vestnik Khirurgi, Sep. 1986, pp. 18-21 and 6 page English translation thereof.
Davydov, Yu. A., et al.; "Vacuum Therapy in the Treatment of Purulent Lactation Mastitis"; Vestnik Khirurgi, May 14, 1986, pp. 66-70, and 9 page English translation thereof.
Yusupov. Yu.N., et al; "Active Wound Drainage", Vestnki Khirurgi, vol. 138, Issue 4, 1987, and 7 page English translation thereof.
Davydov, Yu.A., et al; "Bacteriological and Cytological Assessment of Vacuum Therapy for Purulent Wounds"; Vestnik Khirugi, Oct. 1988, pp. 48-52, and 8 page English translation thereof.
Davydov, Yu.A., et al.; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.
Chariker, Mark E., M.D., et al; "Effective Management of incisional and cutaneous fistulae with closed suction wound drainage"; Contemporary Surgery, vol. 34, Jun. 1989, pp. 59-63.
Egnell Minor, Instruction Book, First Edition, 300 7502, Feb. 1975, pp. 24.
Egnell Minor: Addition to the Users Manual Concerning Overflow Protection—Concerns all Egnell Pumps, Feb. 3, 1983, pp. 2.
Svedman, P.: "Irrigation Treatment of Leg Ulcers", The Lancet, Sep. 3, 1983, pp. 532-534.
Chinn, Steven D. et al.: "Closed Wound Suction Drainage", The Journal of Foot Surgery, vol. 24, No. 1, 1985, pp. 76-81.
Arnljots, Bjorn et al.: "Irrigation Treatment in Split-Thickness Skin Grafting of Intractable Leg Ulcers", Scand J. Plast Reconstr. Surg., No. 19, 1985, pp. 211-213.
Svedman, P.: "A Dressing Allowing Continuous Treatment of a Biosurface", IRCS Medical Science: Biomedical Technology, Clinical Medicine, Surgery and Transplantation, vol. 7, 1979, p. 221.
Svedman, P. et al: "A Dressing System Providing Fluid Supply and Suction Drainage Used for Continuous of Intermittent Irrigation", Annals of Plastic Surgery, vol. 17, No. 2, Aug. 1986, pp. 125-133.
N.A. Bagautdinov, "Variant of External Vacuum Aspiration in the Treatment of Purulent Diseases of Soft Tissues," Current Problems in Modern Clinical Surgery: Interdepartmental Collection, edited by V. Ye Volkov et al. (Chuvashia State University, Cheboksary, U.S.S.R. 1986); pp. 94-96 (copy and certified translation).
K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.
G. Živadinovi?, V. ?uki?, Ž. Maksimovi?, ?. Radak, and p. Peška, "Vacuum Therapy in the Treatment of Peripheral Blood Vessels," Timok Medical Journal 11 (1986), pp. 161-164 (copy and certified translation).
F.E. Johnson, "An Improved Technique for Skin Graft Placement Using a Suction Drain," Surgery, Gynecology, and Obstetrics 159 (1984), pp. 584-585.
A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (copy and certified translation).
M. Schein, R. Saadia, J.R. Jamieson, and G.A.G. Decker, "The 'Sandwich Technique' in the Management of the Open Abdomen," British Journal of Surgery 73 (1986), pp. 369-370.
D.E. Tribble, An Improved Sump Drain-Irrigation Device of Simple Construction, Archives of Surgery 105 (1972) pp. 511-513.
M.J. Morykwas, L.C. Argenta, E.I. Shelton-Brown, and W. McGuirt, "Vacuum-Assisted Closure: A New Method for Wound Control and Treatment: Animal Studies and Basic Foundation," Annals of Plastic Surgery 38 (1997), pp. 553-562 (Morykwas I).
C.E. Tennants, "The Use of Hypermia in the Postoperative Treatment of Lesions of the Extremities and Thorax," Journal of the American Medical Association 64 (1915), pp. 1548-1549.
Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.
V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").

(56) References Cited

OTHER PUBLICATIONS

V.A. Kuznetsov & N.a. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").

V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").

V.A.C. ® Therapy Clinical Guidelines: A Reference Source for Clinicians; Jul. 2007.

Extended European Search Report for Corresponding Application No. 192012706, dated Jan. 23, 2020.

ISR and Written Opinion for corresponding PCT/US2016/062555 dated Apr. 19, 2017.

\* cited by examiner

FLUID MANAGEMENT APPARATUS AND METHOD

RELATED APPLICATIONS

This present invention is the National Stage of International Application No. PCT/US2016/062555, entitled "Fluid Management Apparatus And Method," filed Nov. 17, 2016, and claims the benefit of U.S. Provisional Patent Application No. 62/257,292, entitled "Fluid Management Apparatus And Method," filed Nov. 19, 2015, all of which are incorporated herein by reference for all purposes.

TECHNICAL FIELD

The invention set forth in the appended claims relates generally to tissue treatment systems and more particularly, but without limitation, to apparatuses and methods for managing fluid and blockages in tissue treatment systems.

BACKGROUND

Clinical studies and practice have shown that reducing pressure in proximity to a tissue site can augment and accelerate growth of new tissue at the tissue site. The applications of this phenomenon are numerous, but it has proven particularly advantageous for treating wounds. Regardless of the etiology of a wound, whether trauma, surgery, or another cause, proper care of the wound is important to the outcome. Treatment of wounds or other tissue with reduced pressure may be commonly referred to as "negative-pressure therapy," but is also known by other names, including "negative-pressure wound therapy," "reduced-pressure therapy," "vacuum therapy," "vacuum-assisted closure," and "topical negative-pressure," for example. Negative-pressure therapy may provide a number of benefits, including migration of epithelial and subcutaneous tissues, improved blood flow, and micro-deformation of tissue at a wound site. Together, these benefits can increase development of granulation tissue and reduce healing times.

While the clinical benefits of negative-pressure therapy are widely known, improvements to therapy systems, components, and processes continues may benefit healthcare providers and patients.

BRIEF SUMMARY

New and useful systems, apparatuses, and methods for managing fluid in a negative-pressure therapy environment are set forth in the appended claims. Illustrative embodiments are also provided to enable a person skilled in the art to make and use the claimed subject matter.

In some embodiments, a vibration apparatus can augment and enhance negative-pressure therapy systems. For example, the apparatus can be attached to an external surface of a dressing, fluid conductor, or other components. The apparatus can be actuated to generate low-amplitude vibrations, which can be transmitted through the components. In some embodiments, the apparatus can be actuated by a controller based on pressure, time, or other operating parameter. In other embodiments, the apparatus may be pneumatically actuated based on pressure changes. Kinetic energy of the oscillations can agitate fluid in the components, which can lower the viscosity of the fluid and reduce the frequency of blockages in fluid conductors. Vibrations may also agitate a tissue site, which can encourage blood flow and granulation.

In some example embodiments, the vibrations may be generated by a vibration motor. For example, the apparatus may include a circuit comprising a vibration motor coupled to a low-frequency astable oscillator. The motor preferably provides a normalized amplitude in a range of about 0.7-1.9 G, and can be powered by direct current from a small battery to make the apparatus self-contained and disposable.

In some embodiments, the circuit may be controlled by a single-pole pressure switch, which preferably comprises a moving diaphragm configured to open and close electrical contacts with the motor. The device can be mounted so that an inlet orifice for the pressure switch is fluidly coupled to a negative-pressure source. For example, the inlet may be aligned with an aperture in a dressing to allow the switch to be actuated by pressure in the dressing. Additionally or alternatively, the apparatus may be coupled to a dressing interface that connects the dressing with a fluid conductor. A tee-fitting or micro-needle can fluidly couple the switch to negative-pressure in the dressing interface or fluid conductor, for example. A filter may be integrated over the inlet to prevent contaminants from entering the switch.

A controlling oscillator can be used to extend battery life by running the motor on an intermittent duty cycle. For example, in some embodiments, the pressure switch may be configured to close electrical contacts and turn on the circuit if negative-pressure is applied to a dressing, and the motor may vibrate on a low duty-cycle while negative-pressure is applied to a dressing. Applying intermittent negative pressure may prolong battery life at a rate determined by the therapy duty cycle. If continuous therapy is applied, an astable oscillator can determine the power consumption.

More generally, an apparatus for managing fluid in a negative-pressure environment may comprise an agitator, which may include a pressure switch, a vibration motor, and an electrical energy source. The pressure switch may comprise an input aperture, electrical contacts, and a piston configured to open and close the electrical contacts based on a pressure in the input aperture. The vibration motor and electrical energy source may be coupled to the electrical contacts. In some embodiments, the piston may be a flexible diaphragm. The apparatus may additionally comprise a spring configured to bias the piston against negative pressure in the input aperture. Some embodiments may include a vibration motor, and an astable oscillator may be coupled to the vibration motor. The astable oscillator may be configured to activate and de-activate the motor while the electrical contacts of the pressure switch are closed, for example.

Additionally or alternatively, other example embodiments may comprise a negative-pressure source and one or more distribution components, such as a dressing or a tube. An agitator may be configured to be coupled to a distribution component, and may be operable to generate vibrations in the distribution component.

A method of managing fluid in a negative-pressure therapy apparatus is also described herein, wherein some example embodiments include delivering negative pressure to a distribution component and agitating the distribution component, which can reduce viscosity of exudate. For example, in some embodiments, the distribution component may be agitated when negative pressure is delivered to the distribution component. Agitation may comprise selectively providing vibration when negative-pressure is delivered. For example, a vibration motor may be intermittently activated for predetermined intervals when negative-pressure is delivered to the distribution component.

Additionally or alternatively, a method of treating a tissue site with negative pressure is described. In some embodiments, the method may comprise fluidly coupling a negative-pressure source to a distribution component, such as a dressing or a fluid conductor; coupling a vibration motor to the distribution component; and delivering negative-pressure from the negative-pressure source to the distribution component. The vibration motor may be actuated to generate vibrations, which can be transmitted through the distribution component. In some embodiments, the vibration motor may be electrically coupled to a switch, and the method may further comprise fluidly coupling the switch to the negative-pressure source and pneumatically actuating the switch to operate the vibration motor.

Objectives, advantages, and a preferred mode of making and using the claimed subject matter may be understood best by reference to the accompanying drawings in conjunction with the following detailed description of illustrative embodiments.

DESCRIPTION OF EXAMPLE EMBODIMENTS

The following description of example embodiments provides information that enables a person skilled in the art to make and use the subject matter set forth in the appended claims, but may omit certain details already well-known in the art. The following detailed description is, therefore, to be taken as illustrative and not limiting.

The example embodiments may also be described herein with reference to spatial relationships between various elements or to the spatial orientation of various elements depicted in the attached drawings. In general, such relationships or orientation assume a frame of reference consistent with or relative to a patient in a position to receive treatment. However, as should be recognized by those skilled in the art, this frame of reference is merely a descriptive expedient rather than a strict prescription.

Figure 1:
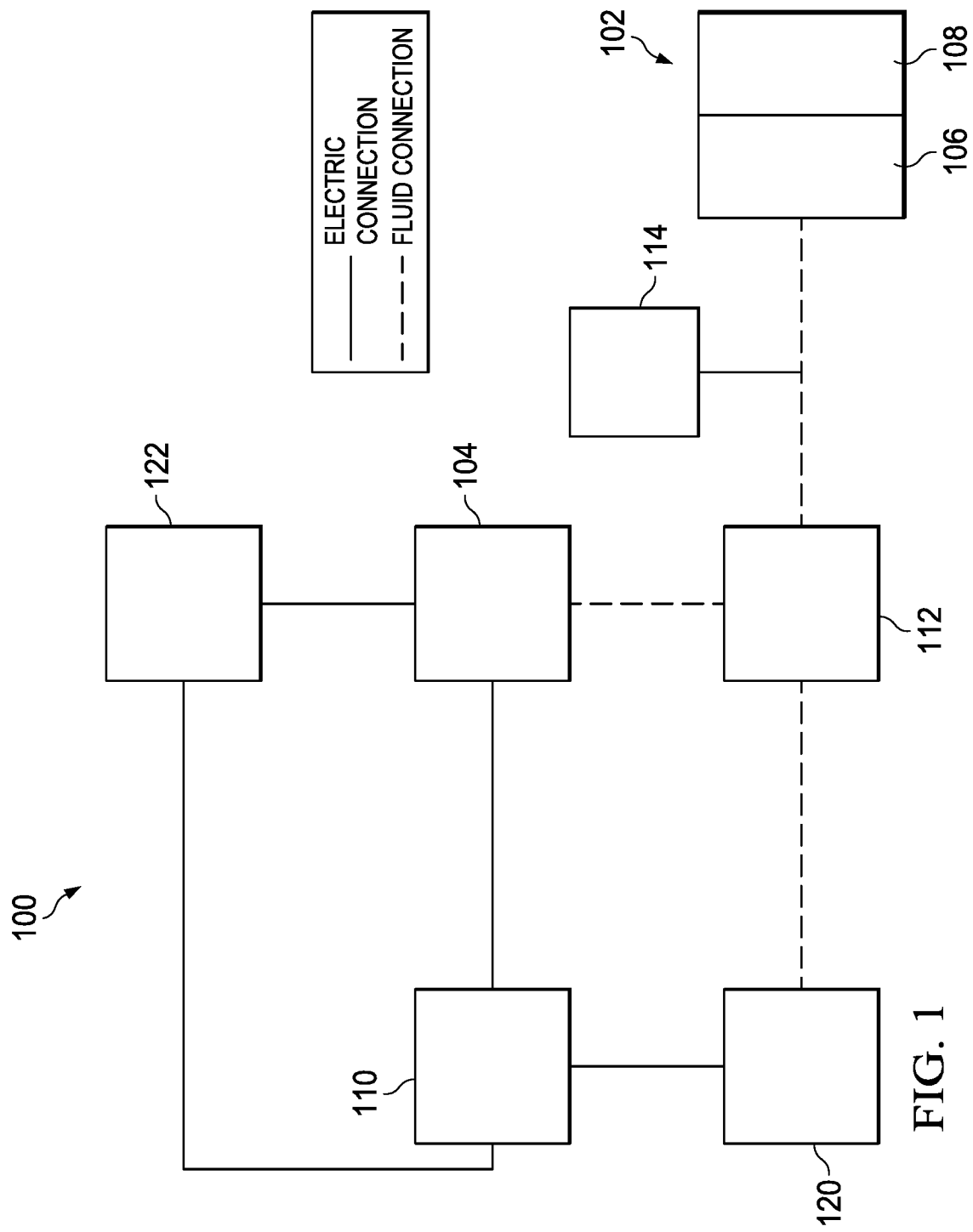
FIG. 1 is a functional block diagram of an example embodiment of a therapy system that can provide negative-pressure therapy or treatment to a tissue site in accordance with this specification.

FIG. 1 is a simplified functional block diagram of an example embodiment of a therapy system 100 that can provide negative-pressure therapy or treatment to a tissue site in accordance with this specification.

The term "tissue site" in this context broadly refers to a wound, defect, or other treatment target located on or within tissue, including but not limited to, bone tissue, adipose tissue, muscle tissue, neural tissue, dermal tissue, vascular tissue, connective tissue, cartilage, tendons, or ligaments. A wound may include chronic, acute, traumatic, subacute, and dehisced wounds, partial-thickness burns, ulcers (such as diabetic, pressure, or venous insufficiency ulcers), flaps, and grafts, for example. The term "tissue site" may also refer to areas of any tissue that are not necessarily wounded or defective, but are instead areas in which it may be desirable to add or promote the growth of additional tissue. For example, negative pressure may be applied to a tissue site to grow additional tissue that may be harvested and transplanted.

The therapy system 100 may include a negative-pressure supply, and may include or be configured to be coupled to a distribution component, such as a dressing. In general, a distribution component may refer to any complementary or ancillary component configured to be fluidly coupled to a negative-pressure supply in a fluid path between a negative-pressure supply and a tissue site. A distribution component is preferably detachable, and may be disposable, reusable, or recyclable. For example, a dressing 102 may be fluidly coupled to a negative-pressure source 104, as illustrated in FIG. 1. A dressing may include a cover, a tissue interface, or both in some embodiments. The dressing 102, for example, may include a cover 106 and a tissue interface 108. A regulator or a controller, such as a controller 110, may also be coupled to the negative-pressure source 104.

In some embodiments, a dressing interface may facilitate coupling the negative-pressure source 104 to the dressing 102. For example, such a dressing interface may be a T.R.A.C.® Pad or Sensa T.R.A.C.® Pad available from KCI of San Antonio, Tex. The therapy system 100 may optionally include a fluid container, such as a container 112, coupled to the dressing 102 and to the negative-pressure source 104.

Additionally, the therapy system 100 may include sensors to measure operating parameters and provide feedback signals to the controller 110 indicative of the operating parameters. As illustrated in FIG. 1, for example, the therapy system 100 may include a pressure sensor 120, an electric sensor 122, or both, coupled to the controller 110. The pressure sensor 120 may also be coupled or configured to be coupled to a distribution component and to the negative-pressure source 104.

The therapy system 100 may additionally include one or more agitators coupled to a distribution component. In some embodiments, an agitator may be actuated by the controller 110 based on feedback from the pressure sensor 120, for example. In other embodiments, an agitator may also be fluidly coupled to a negative-pressure source, such as the negative-pressure source 104, and can be actuated by pressure changes. For example, in some embodiments, an agitator 114 may be fluidly coupled in-line between the dressing 102 and the container 112, as illustrated in FIG. 1. The agitator 114 is generally adapted to generate vibrations and transmit the vibrations to distribution components.

Components may be fluidly coupled to each other to provide a path for transferring fluids (i.e., liquid and/or gas) between the components. For example, components may be fluidly coupled through a fluid conductor, such as a tube. A "tube," as used herein, broadly includes a tube, pipe, hose, conduit, or other structure with one or more lumina adapted to convey a fluid between two ends. Typically, a tube is an elongated, cylindrical structure with some flexibility, but the geometry and rigidity may vary. In some embodiments, components may also be coupled by virtue of physical proximity, being integral to a single structure, or being formed from the same piece of material. Moreover, some fluid conductors may be molded into or otherwise integrally combined with other components. Coupling may also include mechanical, thermal, electrical, or chemical coupling (such as a chemical bond) in some contexts. For example, a tube may mechanically and fluidly couple the dressing 102 to the container 112 in some embodiments.

In general, components of the therapy system 100 may be coupled directly or indirectly. For example, the negative-pressure source 104 may be directly coupled to the controller 110, and may be indirectly coupled to the dressing 102 through the container 112.

The fluid mechanics of using a negative-pressure source to reduce pressure in another component or location, such as within a sealed therapeutic environment, can be mathematically complex. However, the basic principles of fluid mechanics applicable to negative-pressure therapy are generally well-known to those skilled in the art, and the process of reducing pressure may be described illustratively herein as "delivering," "distributing," or "generating" negative pressure, for example.

In general, exudates and other fluids flow toward lower pressure along a fluid path. Thus, the term "downstream" typically implies something in a fluid path relatively closer to a source of negative pressure or further away from a source of positive pressure. Conversely, the term "upstream" implies something relatively further away from a source of negative pressure or closer to a source of positive pressure. Similarly, it may be convenient to describe certain features in terms of fluid "inlet" or "outlet" in such a frame of reference. This orientation is generally presumed for purposes of describing various features and components herein. However, the fluid path may also be reversed in some applications (such as by substituting a positive-pressure source for a negative-pressure source) and this descriptive convention should not be construed as a limiting convention.

"Negative pressure" generally refers to a pressure less than a local ambient pressure, such as the ambient pressure in a local environment external to a sealed therapeutic environment provided by the dressing 102. In many cases, the local ambient pressure may also be the atmospheric pressure at which a tissue site is located. Alternatively, the pressure may be less than a hydrostatic pressure associated with tissue at the tissue site. Unless otherwise indicated, values of pressure stated herein are gauge pressures. Similarly, references to increases in negative pressure typically refer to a decrease in absolute pressure, while decreases in negative pressure typically refer to an increase in absolute pressure. While the amount and nature of negative pressure applied to a tissue site may vary according to therapeutic requirements, the pressure is generally a low vacuum, also commonly referred to as a rough vacuum, between −5 mm Hg (−667 Pa) and −500 mm Hg (−66.7 kPa). Common therapeutic ranges are between −75 mm Hg (−9.9 kPa) and −300 mm Hg (−39.9 kPa).

A negative-pressure supply, such as the negative-pressure source 104, may be a reservoir of air at a negative pressure, or may be a manual or electrically-powered device that can reduce the pressure in a sealed volume, such as a vacuum pump, a suction pump, a wall suction port available at many healthcare facilities, or a micro-pump, for example. A negative-pressure supply may be housed within or used in conjunction with other components, such as sensors, processing units, alarm indicators, memory, databases, software, display devices, or user interfaces that further facilitate therapy. For example, in some embodiments, the negative-pressure source 104 may be combined with the controller 110 and other components into a therapy unit. A negative-pressure supply may also have one or more supply ports configured to facilitate coupling and de-coupling the negative-pressure supply to one or more distribution components.

The tissue interface 108 can be generally adapted to contact a tissue site. The tissue interface 108 may be partially or fully in contact with the tissue site. If the tissue site is a wound, for example, the tissue interface 108 may partially or completely fill the wound, or may be placed over the wound. The tissue interface 108 may take many forms, and may have many sizes, shapes, or thicknesses depending on a variety of factors, such as the type of treatment being implemented or the nature and size of a tissue site. For example, the size and shape of the tissue interface 108 may be adapted to the contours of deep and irregular shaped tissue sites. Moreover, any or all of the surfaces of the tissue interface 108 may have projections or an uneven, course, or jagged profile that can induce strains and stresses on a tissue site, which can promote granulation at the tissue site.

In some embodiments, the tissue interface 108 may be a manifold. A "manifold" in this context generally includes any substance or structure providing a plurality of pathways adapted to collect or distribute fluid across a tissue site under pressure. For example, a manifold may be adapted to receive negative pressure from a source and distribute negative pressure through multiple apertures across a tissue site, which may have the effect of collecting fluid from across a tissue site and drawing the fluid toward the source. In some embodiments, the fluid path may be reversed or a secondary fluid path may be provided to facilitate delivering fluid across a tissue site.

In some illustrative embodiments, the pathways of a manifold may be interconnected to improve distribution or collection of fluids across a tissue site. In some illustrative embodiments, a manifold may be a porous foam material having interconnected cells or pores. For example, cellular foam, open-cell foam, reticulated foam, porous tissue collections, and other porous material such as gauze or felted mat generally include pores, edges, and/or walls adapted to form interconnected fluid channels. Liquids, gels, and other foams may also include or be cured to include apertures and fluid pathways. In some embodiments, a manifold may additionally or alternatively comprise projections that form interconnected fluid pathways. For example, a manifold may be molded to provide surface projections that define interconnected fluid pathways.

The average pore size of a foam may vary according to needs of a prescribed therapy. For example, in some embodiments, the tissue interface 108 may be a foam having pore sizes in a range of 400-600 microns. The tensile strength of the tissue interface 108 may also vary according to needs of a prescribed therapy. For example, the tensile strength of a foam may be increased for instillation of topical treatment solutions. In one non-limiting example, the tissue interface 108 may be an open-cell, reticulated polyurethane foam such as GranuFoam® dressing or VeraFlo® foam, both available from Kinetic Concepts, Inc. of San Antonio, Tex.

The tissue interface 108 may be either hydrophobic or hydrophilic. In an example in which the tissue interface 108 may be hydrophilic, the tissue interface 108 may also wick fluid away from a tissue site, while continuing to distribute negative pressure to the tissue site. The wicking properties of the tissue interface 108 may draw fluid away from a tissue site by capillary flow or other wicking mechanisms. An example of a hydrophilic foam is a polyvinyl alcohol, open-cell foam such as V.A.C. WhiteFoam® dressing available from Kinetic Concepts, Inc. of San Antonio, Tex. Other hydrophilic foams may include those made from polyether.

Other foams that may exhibit hydrophilic characteristics include hydrophobic foams that have been treated or coated to provide hydrophilicity.

The tissue interface 108 may further promote granulation at a tissue site when pressure within the sealed therapeutic environment is reduced. For example, any or all of the surfaces of the tissue interface 108 may have an uneven, coarse, or jagged profile that can induce microstrains and stresses at a tissue site if negative pressure is applied through the tissue interface 108.

In some embodiments, the tissue interface 108 may be constructed from bioresorbable materials. Suitable bioresorbable materials may include, without limitation, a polymeric blend of polylactic acid (PLA) and polyglycolic acid (PGA). The polymeric blend may also include without limitation polycarbonates, polyfumarates, and capralactones. The tissue interface 108 may further serve as a scaffold for new cell-growth, or a scaffold material may be used in conjunction with the tissue interface 108 to promote cell-growth. A scaffold is generally a substance or structure used to enhance or promote the growth of cells or formation of tissue, such as a three-dimensional porous structure that provides a template for cell growth. Illustrative examples of scaffold materials include calcium phosphate, collagen, PLA/PGA, coral hydroxy apatites, carbonates, or processed allograft materials.

In some embodiments, the cover 106 may provide a bacterial barrier and protection from physical trauma. The cover 106 may also be constructed from a material that can reduce evaporative losses and provide a fluid seal between two components or two environments, such as between a therapeutic environment and a local external environment. The cover 106 may be, for example, an elastomeric film or membrane that can provide a seal adequate to maintain a negative pressure at a tissue site for a given negative-pressure source. The cover 106 may have a high moisture-vapor transmission rate (MVTR) in some applications. For example, the MVTR may be at least 300 g/m^2 per twenty-four hours in some embodiments. In some example embodiments, the cover 106 may be a polymer drape, such as a polyurethane film, that is permeable to water vapor but impermeable to liquid. Such drapes typically have a thickness in the range of 25-50 microns. For permeable materials, the permeability generally should be low enough that a desired negative pressure may be maintained.

An attachment device may be used to attach the cover 106 to an attachment surface, such as undamaged epidermis, a gasket, or another cover. The attachment device may take many forms. For example, an attachment device may be a medically-acceptable, pressure-sensitive adhesive that extends about a periphery, a portion, or an entire sealing member. In some embodiments, for example, some or all of the cover 106 may be coated with an acrylic adhesive having a coating weight between 25-65 grams per square meter (g.s.m.). Thicker adhesives, or combinations of adhesives, may be applied in some embodiments to improve the seal and reduce leaks. Other example embodiments of an attachment device may include a double-sided tape, paste, hydrocolloid, hydrogel, silicone gel, or organogel.

A controller, such as the controller 110, may be a microprocessor or computer programmed to operate one or more components of the therapy system 100, such as the negative-pressure source 104. In some embodiments, for example, the controller 110 may be a microcontroller, which generally comprises an integrated circuit containing a processor core and a memory programmed to directly or indirectly control one or more operating parameters of the therapy system 100. Operating parameters may include the power applied to the negative-pressure source 104, the pressure generated by the negative-pressure source 104, or the pressure distributed to the tissue interface 108, for example. The controller 110 is also preferably configured to receive one or more input signals, such as a feedback signal, and programmed to modify one or more operating parameters based on the input signals.

Sensors, such as the pressure sensor 120 or the electric sensor 122, are generally known in the art as any apparatus operable to detect or measure a physical phenomenon or property, and generally provide a signal indicative of the phenomenon or property that is detected or measured. For example, the pressure sensor 120 and the electric sensor 122 may be configured to measure one or more operating parameters of the therapy system 100. In some embodiments, the pressure sensor 120 may be a transducer configured to measure pressure in a pneumatic pathway and convert the measurement to a signal indicative of the pressure measured. In some embodiments, for example, the pressure sensor 120 may be a piezoresistive strain gauge. The electric sensor 122 may optionally measure operating parameters of the negative-pressure source 104, such as the voltage or current, in some embodiments. Preferably, the signals from the pressure sensor 120 and the electric sensor 122 are suitable as an input signal to the controller 110, but some signal conditioning may be appropriate in some embodiments. For example, the signal may need to be filtered or amplified before it can be processed by the controller 110. Typically, the signal is an electrical signal, but may be represented in other forms, such as an optical signal.

The container 112 is representative of a container, canister, pouch, or other storage component, which can be used to manage exudates and other fluids withdrawn from a tissue site. In many environments, a rigid container may be preferred or required for collecting, storing, and disposing of fluids. In other environments, fluids may be properly disposed of without rigid container storage, and a re-usable container could reduce waste and costs associated with negative-pressure therapy.

Figure 2:
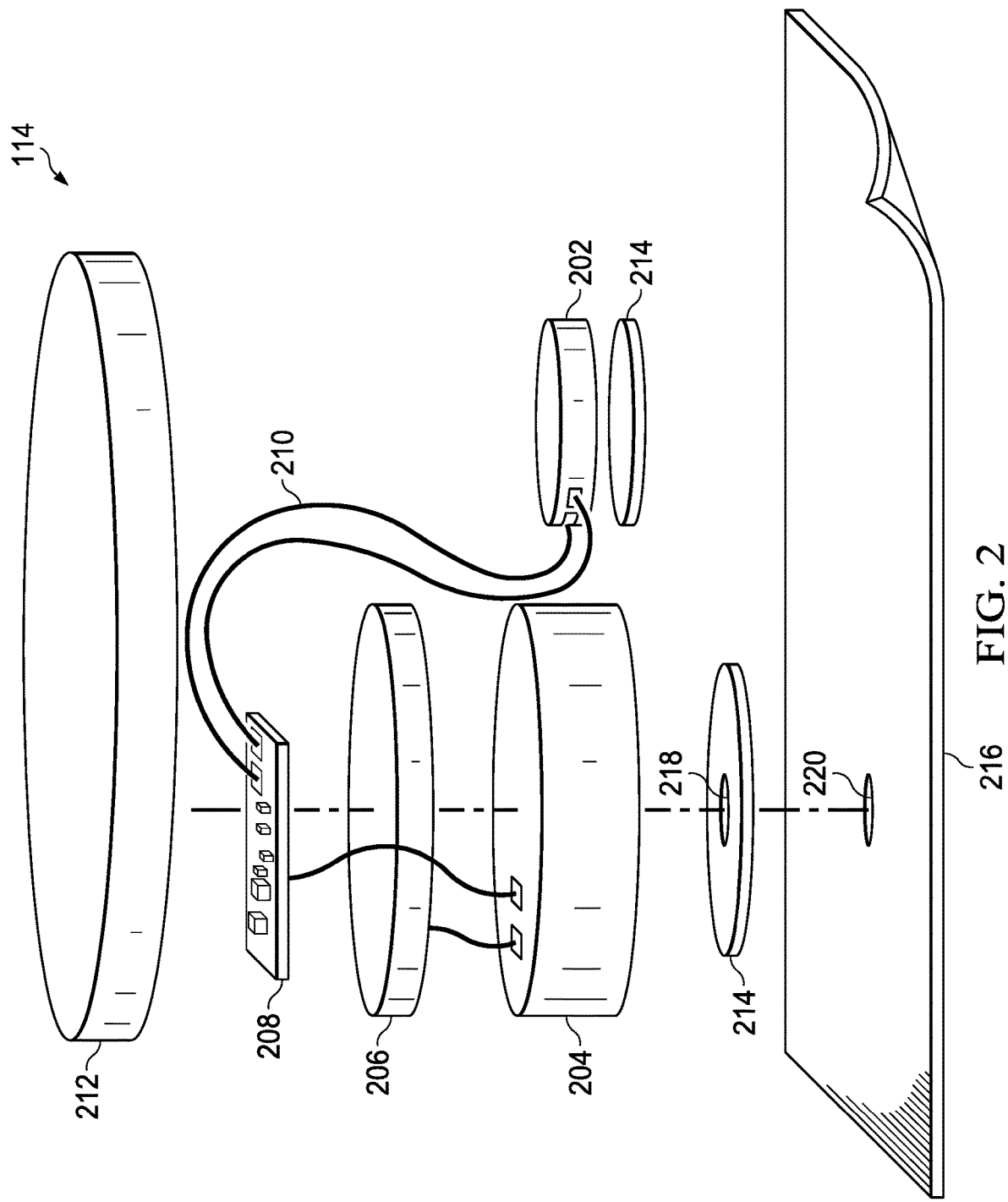
FIG. 2 is a schematic diagram illustrating additional details of an agitator that may be associated with some embodiments of the therapy system of FIG. 1.

FIG. 2 is a schematic diagram illustrating additional details that may be associated with some example embodiments of the agitator 114. The components in the example of FIG. 2 are exploded for illustration purposes. In the example embodiment of FIG. 2, the agitator 114 generally includes a vibration motor 202, a switch 204, a battery 206, and a circuit board 208. Electrical conductors 210 may electrically couple the vibration motor 202 to the switch 204 through the circuit board 208. In some embodiments, the agitator 114 may additionally include a housing 212. The housing 212 may enclose some or all of the components. For example, in some embodiments, the housing 212 may cover the vibration motor 202, the switch 204, the battery 206, and the circuit board 208. In other embodiments, the housing 212 may enclose the battery 206 and the circuit board 208, and be configured to be coupled to the switch 204. In still other example embodiments, the vibration motor 202 may be tethered to the circuit board 208 outside the housing 212. The agitator may also include one or more attachment devices in some embodiments. For example, a first attachment device 214 and a second attachment device 214 are illustrated in the embodiment of FIG. 2. In some embodiments, the first attachment device 214 may be a double-sided adhesive disk adapted to mechanically couple the vibration motor 202 to a dressing 216, and the second attachment device 214 may be a double-sided disk adapted to mechanically couple the switch 204 to the dressing 216. The second attachment device 214 may also include an aperture 218, through which the switch 204 may be fluidly coupled to other components. For example, as illustrated in the embodiment of FIG. 2, the aperture 218 may be aligned with an aperture 220 in the dressing 216 to fluidly couple the switch 204 to the dressing 216.

The vibration motor 202 may be a coin vibration motor, having a diameter of less than 10 millimeters in some embodiments. Normalized amplitude in a range of about 0.7-1.9 G may be suitable for some embodiments. The switch 204 may be a single-pole pressure switch in some embodiments. As illustrated in the example embodiment of FIG. 2, the switch 204 may be disposed at the base of the agitator 114. The battery 206 may be a conventional coin cell battery in some embodiments, and a paper pull-tab (not shown) may isolate the battery 206 until deployed. The circuit board 208 may include a low-frequency astable oscillator control circuit configured to drive the vibration motor 202.

Figure 3:
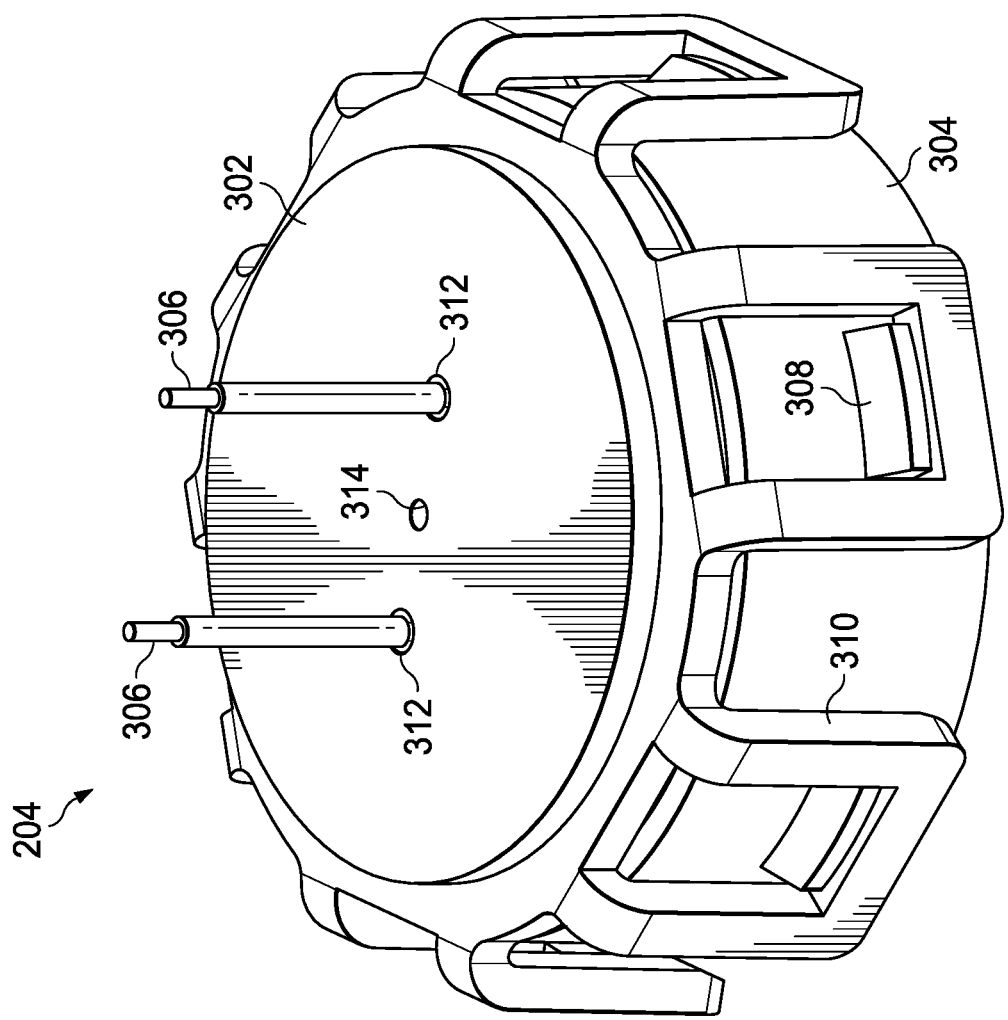
FIG. 3 is a perspective view of an example embodiment of a switch that may be associated with some embodiments of the agitator of FIG. 2.

FIG. 3 is a perspective view of an example embodiment of the switch 204. In the example embodiment of FIG. 3, the switch 204 can generally include a first enclosure 302, a second enclosure 304, and electrical conductors 306. One of the conductors 306 may be coupled to a battery, such as the battery 206 of FIG. 2, and the other may be coupled to a circuit board, such as the circuit board 208. The first enclosure 302 may be coupled to the second enclosure 304 with suitable fasteners. For example, as shown in the example of FIG. 3, the second enclosure 304 may comprise one or more latches 308 adapted to engage corresponding keepers 310 coupled to the first enclosure 302. The electrical conductors 306 may pass through the first enclosure 302 through one or more suitable apertures, such as the apertures 312 of FIG. 3. The switch 204 may also include one or more pressure orifices, such as the pressure orifice 314.

Figure 4:
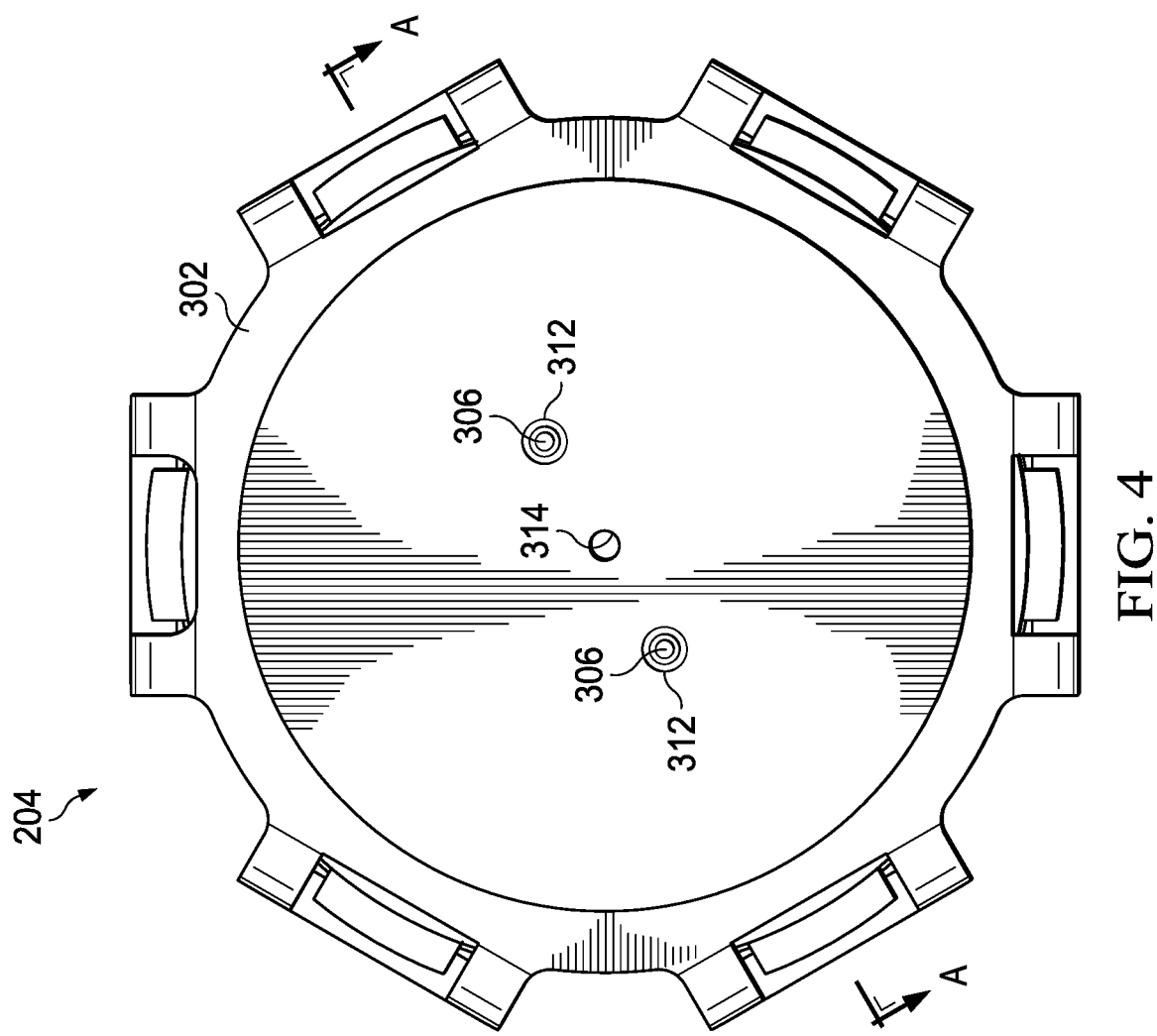
FIG. 4 is a top view of the example switch of FIG. 3.

FIG. 4 is a top view of the switch 204 of FIG. 3, illustrating additional details that may be associated with some embodiments, including position and alignment of the apertures 312, the conductors 306, and the pressure orifice 314.

Figure 5:
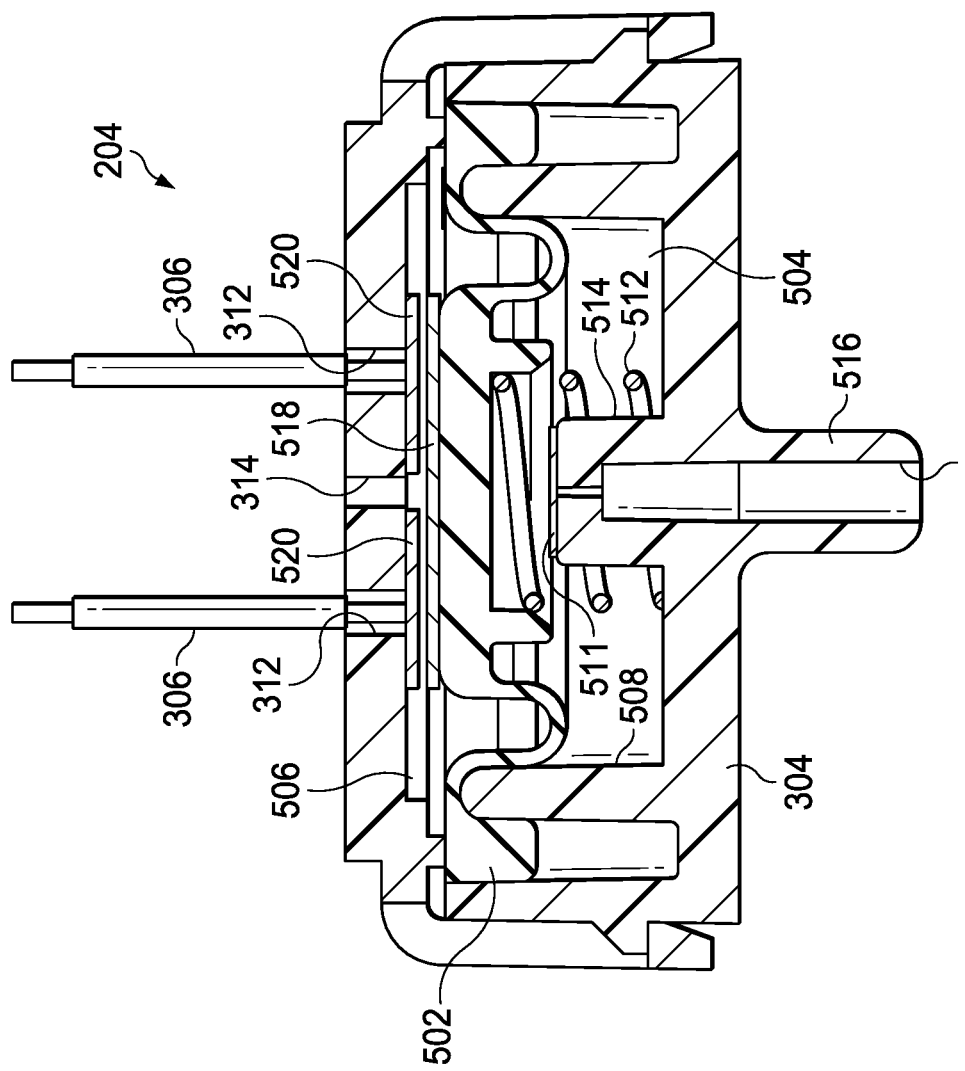
FIG. 5 is a section view of the switch of FIG. 4.

FIG. 5 is a section view of the switch 204 of FIG. 4 taken along line A-A, illustrating additional details that may be associated with some embodiments. As shown in the example of FIG. 5, the switch 204 may include a piston, such as a diaphragm 502, configured to flex or reciprocate within the interior of the switch. Assembled as shown in FIG. 5, the diaphragm 502 may partition the interior of the switch 204 into a first chamber 504 and a second chamber 506. Moreover, the diaphragm 502 may engage the first enclosure 302 or the second enclosure 304 to provide a seal between the first chamber 504 and the second chamber 506. For example, the second enclosure 304 may include a retention support 508 configured to engage the diaphragm 502 and fluidly isolate the first chamber 504 from the second chamber 506. The first chamber 504 and the second chamber 506 are also preferably fluidly isolated from the external environment, except through an aperture 510 and the pressure orifice 314, respectively. In some embodiments, a hydrophobic filter 511 may be disposed between the aperture 510 and the first chamber 504 to substantially reduce or prevent liquid transfer between the aperture 510 and the first chamber 504 while allowing gas transfer.

A spring 512 may also be disposed in the first chamber 504 between the diaphragm 502 and the second enclosure 304. In some embodiments, the spring 512 may bias the diaphragm 502 away from the aperture 510. For example, a first end of the spring 512 may be coupled to a retention boss 514 to restrict lateral movement, and a second end of the spring 512 may be coupled to the diaphragm 502, as shown in FIG. 5. The aperture 510 may extend through the retention boss 514.

In some examples, the second enclosure 304 may also include a port 516. The port 516 is generally configured to be coupled to another fluid conductor or other distribution component. For example, the port 516 may protrude from the second enclosure 304 and have a profile suitable for mechanically coupling to a fitting. The aperture 510 may also pass through the port 516 to fluidly couple the first chamber 504 to a distribution component.

The switch 204 may also include electrically conductive contacts. In the example embodiment of FIG. 5, a contact 518 may be disposed in the second chamber 506 and coupled to the diaphragm 502, and a contact 520 may be electrically coupled to each of the conductors 306. In an open state, the contacts 520 are electrically insulated from each other. For example, in the embodiment illustrated in FIG. 5, the contacts 520 are electrically insulated by air in a gap between them. In a closed state, the contact 518 electrically couples the contacts 520. The diaphragm 502 may be configured to move the contact 518 in some embodiments. For example, assembled as shown in FIG. 5, the contact 518 may be directly coupled to the diaphragm 502 and configured to move with the diaphragm 502. The spring 512 may be configured to bias the diaphragm 502 toward the contacts 520 so that the switch 204 is normally closed. The switch 204 can be opened, for example, if a pressure differential across the diaphragm 502 is sufficiently large to overcome the force of the spring 512 on the diaphragm 502 and move the contact 518 away from the contacts 520. In general, the pressure differential at which the diaphragm 502 moves preferably corresponds to a threshold negative pressure in the first chamber 504. In some embodiments, the switch 204 may include an adjustment screw to adjust tension in the spring 512, which can modify the threshold according to a prescribed therapy.

Figure 6:
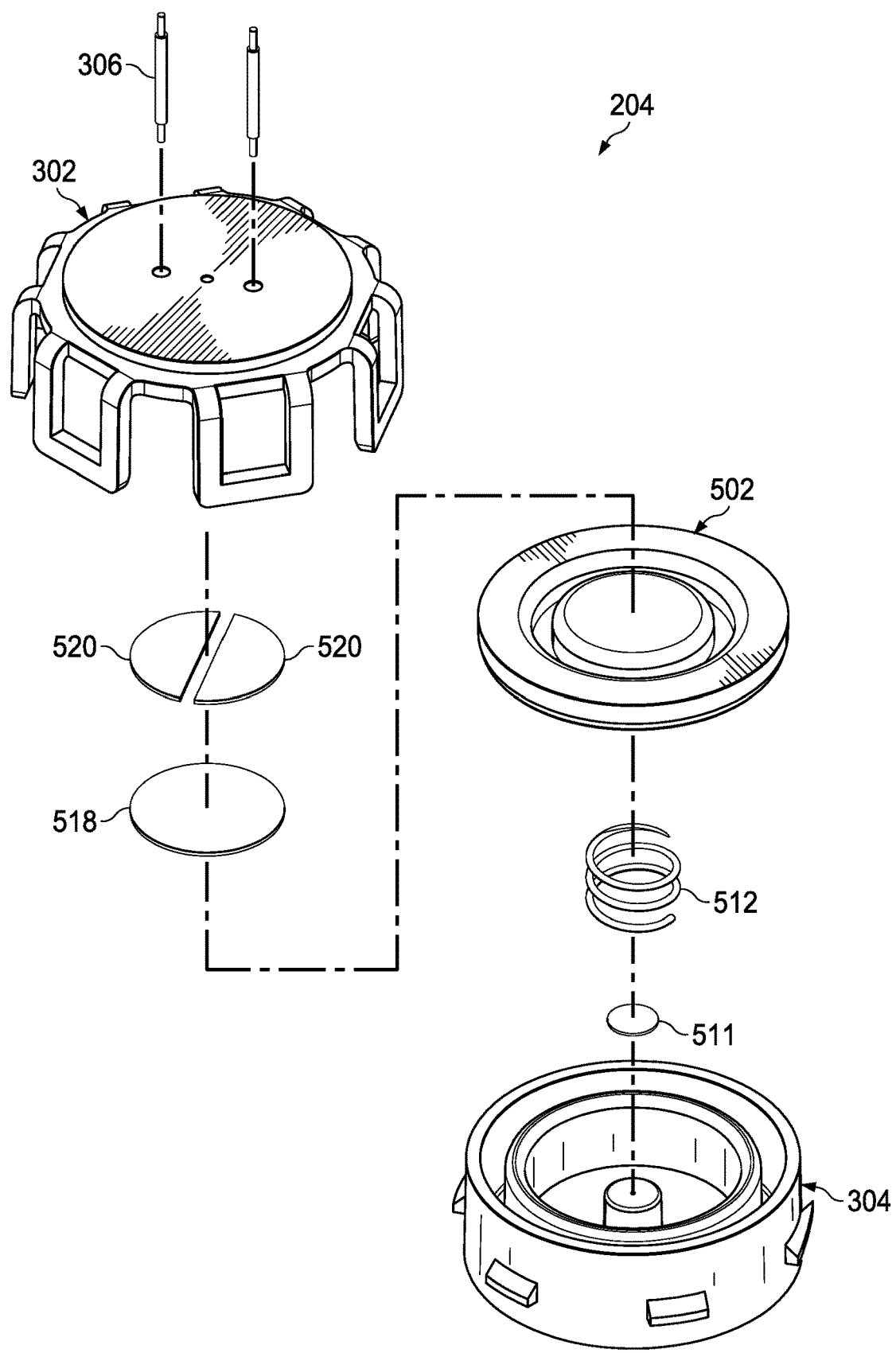
FIG. 6 is an assembly view of the switch of FIG. 5.

FIG. 6 is an assembly view of the switch 204 of FIG. 5, illustrating additional details that may be associated with some embodiments. For example, the contact 518 may be a disk, and the contacts 520 may each be a half of a similarly shaped and sized disk. The diaphragm 502 may also be rounded and sized to fit within the second enclosure 304. The retention support 508 may be an annular support, sized slightly smaller than the diaphragm 502.

The first enclosure 302 and the second enclosure 304 are preferably formed from a material with sufficient rigidity to maintain a substantially constant internal volume under normal operating conditions. For example, a rigid polymer may be suitable for many applications. A polymer may also be advantageous for manufacturing purposes, allowing the first enclosure 302 and the second enclosure 304 to be molded. A diaphragm such as the diaphragm 502 may be constructed from a variety of materials with good damping properties and sufficient flexibility to be responsive to changes in pressure under desired operating conditions. An elastic polymer, such as a high-consistency rubber, may be advantageous for many embodiments. For example, a silicone rubber with a 45-55 shore A hardness and 650% elongation may be suitable for some embodiments.

Figure 7:
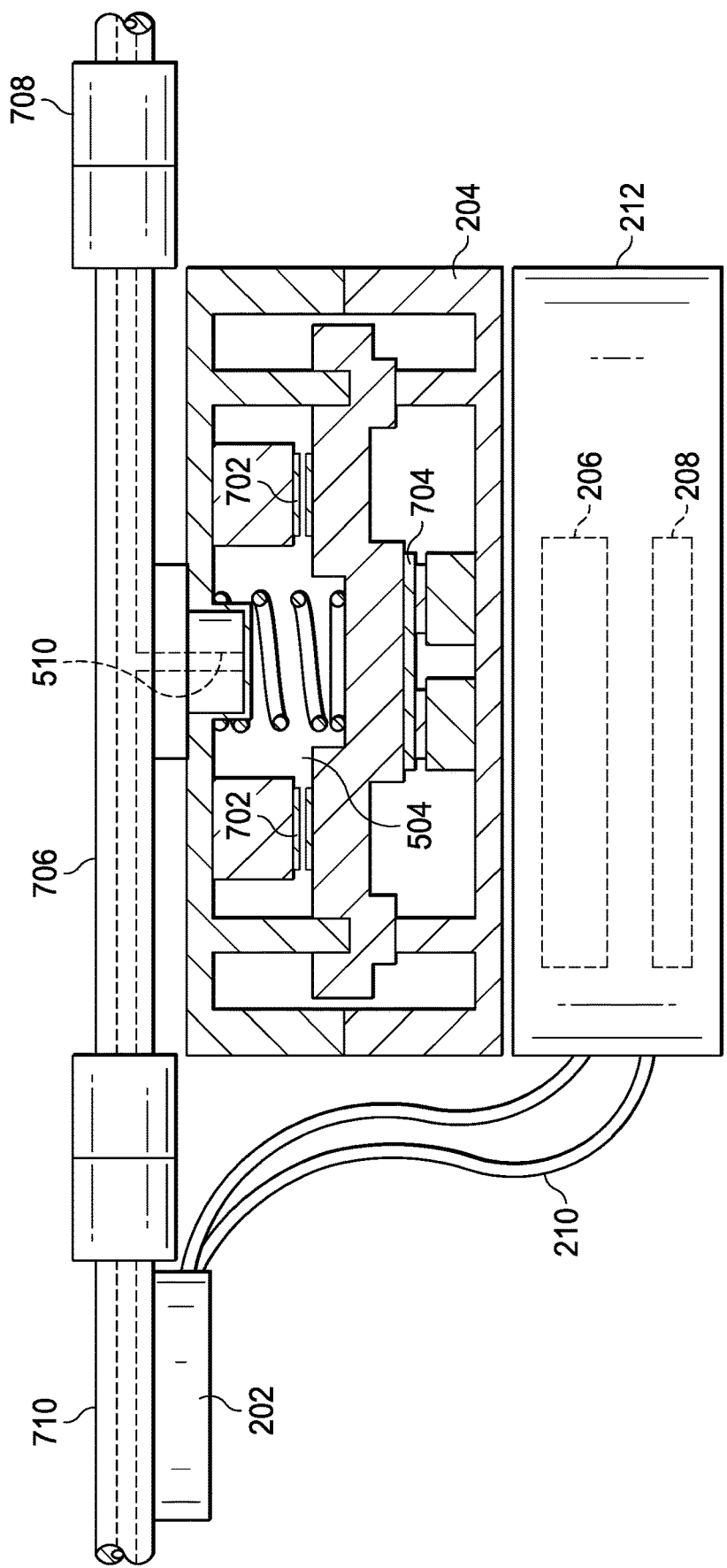
FIG. 7 is a schematic view of another example embodiment of an agitator and a switch.

FIG. 7 is a schematic view of another example embodiment of the agitator 114 and the switch 204. In the example of FIG. 7, the housing 212 may enclose the battery 206 and the circuit board 208. In some embodiments, the switch 204 may include normally open electrical contacts 702 and normally closed electrical contacts 704. The agitator 114 may additionally include or be coupled to a tee fitting 706. For example, in some embodiments, the tee fitting 706 may be pneumatically coupled to the first chamber 504 through the aperture 510. The tee fitting 706 may also couple the first chamber 504 to the negative-pressure source 104 or other downstream distribution component through a connector 708. In the example of FIG. 7, the vibration motor 202 is coupled to a tube 710 upstream of the tee fitting 706.

Figure 8:
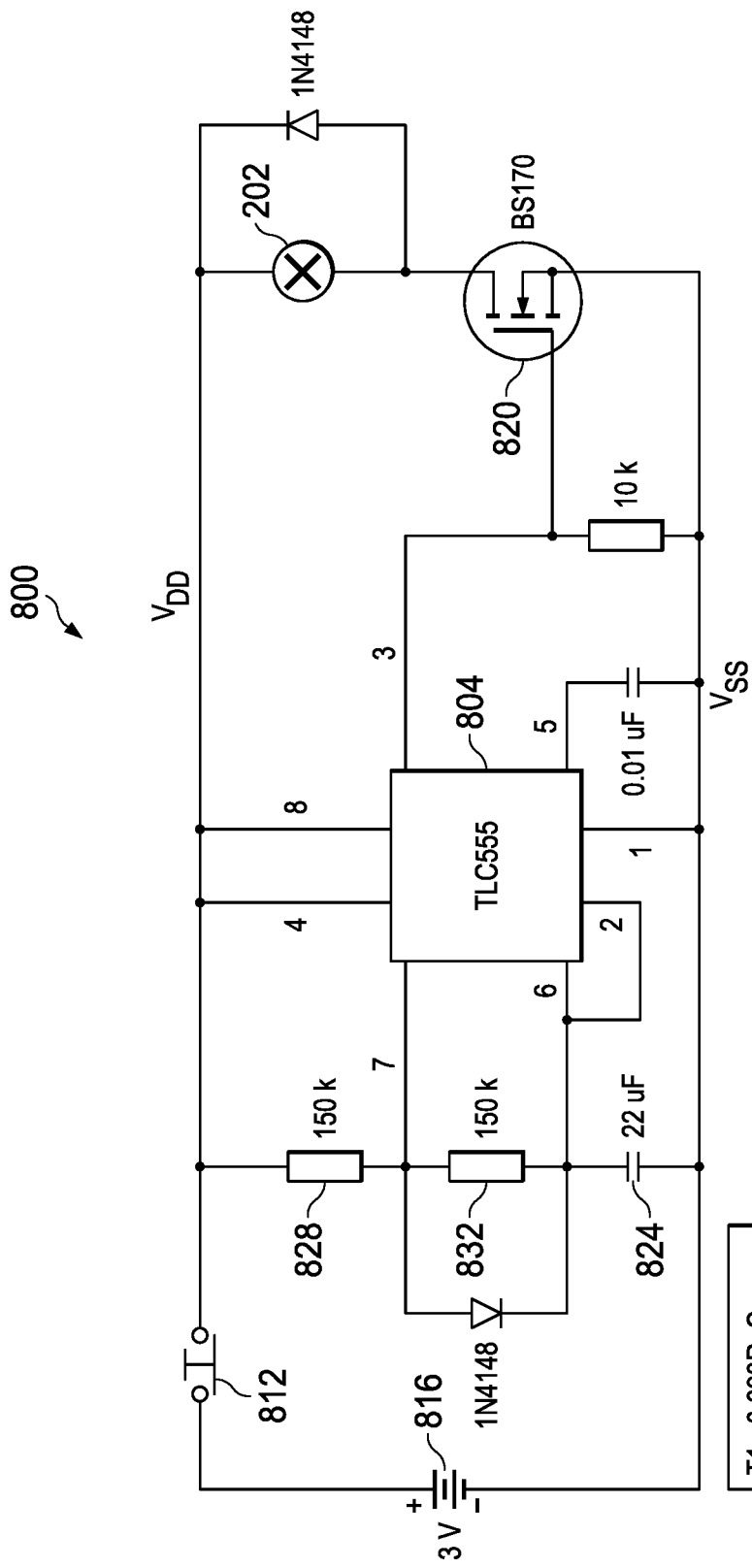
FIG. 8 is a schematic diagram of an example control circuit.

FIG. 8 is a schematic diagram of a control circuit 800, illustrating additional details that may be associated with some embodiments of the circuit board 208. The control circuit 800 may include an oscillator 804, such as a low-frequency astable oscillator, for controlling a vibrating motor, such as the vibrating motor 202. For example, in some embodiments, the oscillator 804 may correspond to a TLC555 LinCMOS timer circuit manufactured by Texas Instruments, but other suitable oscillators may be used. The oscillator 804 (having pins 1-8) can output a repeating high-low signal (e.g., a 1 or 0, respectively) on pin 3 if the switch 812 is closed, in order to selectively turn the motor 808 on and off as described below in more detail. In some embodiments, the switch 812 may correspond to the pressure switch 204, and the on state may correspond to a closed state of the pressure switch 204.

When actuated to an on state, the switch 812 can provide a supply voltage $V_{DD}$ from a battery 816 to the control circuit 800. For example only, the battery 816 may be a 3V coin cell type battery, corresponding to the battery 206. The oscillator 804 can output a high (1) signal on pin 3 to turn on transistor 820 when the supply voltage $V_{DD}$ is received on pins 4 and 8 (i.e., when pins 4 and 8 are high), turning on the motor 808. Conversely, when the switch 812 is actuated to an off state, such as the open state of pressure switch 204, pins 4 and 8 are low, causing the oscillator 804 to output a low (0) signal on pin 3 to turn off the transistor 820 and the motor 808. For example only, pin 4 corresponds to a reset pin and pin 8 corresponds to a supply voltage pin.

The control circuit 800 may be configured to operate the motor 808 at a desired duty cycle (e.g., 50%) while the switch 812 is on. For example, if the switch 812 is on, the control circuit 800 may control the motor 808 to operate at a 50% duty cycle. In the example embodiment of FIG. 8, the duty cycle may be controlled according to inputs and configurations of pins 2, 6, 5, and 7 of the oscillator 804. For example, when the switch 812 is initially turned on, the oscillator 804 turns on the motor 808, pins 2 and 6 receive a first voltage, and capacitor 824 begins to charge. After charging for a first time T1, the capacitor 824 is charged sufficiently to provide a second voltage to pins 2 and 6 (e.g., the first voltage increases above respective thresholds associated with pins 2 and 6 to the second voltage), which causes the oscillator 804 to turn the motor 808 off (by outputting a low, or 0, on pin 3). When the output of the oscillator 804 on pin 3 is low, discharge pin 7 of the oscillator 804 provides a discharge path to ground via ground pin 1 of the oscillator 804, causing the capacitor 824 to discharge. After discharging for a second time T2, the second voltage provided to pins 2 and 6 drops below the respective thresholds of pins 2 and 6, causing the oscillator 804 to turn the motor 808 on and repeat the cycle.

For example only, T1 and T2 may correspond to values of the capacitor 824 and resistors 828 and 832, where the duty cycle of the control circuit 800 corresponds to T1/(T1+T2). To adjust the duty cycle, the respective thresholds of pins 2 and 6 may be adjusted according to a control voltage applied to pin 5 and the values of the capacitor 824 and resistors 828 and 832 may be further adjusted.

In operation, the tissue interface 108 may be placed within, over, on, or otherwise proximate to a tissue site. The cover 106 may be placed over the tissue interface 108 and sealed to an attachment surface near the tissue site. For example, the cover 106 may be sealed to undamaged epidermis peripheral to a tissue site. Thus, the dressing 102 can provide a sealed therapeutic environment proximate to a tissue site, substantially isolated from the external environment, and the negative-pressure source 104 can reduce the pressure in the sealed therapeutic environment. Negative pressure applied across the tissue site through the tissue interface 108 in the sealed therapeutic environment can induce macrostrain and microstrain in the tissue site, as well as remove exudates and other fluids from the tissue site, which can be collected in container 112.

The agitator 114 may be coupled to a distribution component in the fluid path between a tissue site and the negative-pressure source 104. For example, the agitator 114 may be coupled directly to the dressing 102, or may be directly coupled to a tube between the dressing 102 and the negative-pressure source 104. The agitator 114 may also be pneumatically coupled to the negative-pressure source 104, in some embodiments, and can be actuated by pressure changes in the fluid path. In some embodiments, the agitator 114 may be coupled indirectly to the negative-pressure source 104 through an input aperture, such as the aperture 510, so that movement of the diaphragm 502 is based on pressure in the input aperture 510 or the first chamber 504. For example, the aperture 510 may be aligned with an aperture in the cover 106 to fluidly couple the first chamber 504 to negative pressure in the dressing 102. The diaphragm 502 may be biased against negative pressure in the input aperture 510 or the first chamber 504. For example, the spring 512 may bias the diaphragm 502 against negative pressure in the input aperture 510, so that the contacts 520 are closed until negative pressure exceeds a target negative pressure. If the negative pressure is reduced below the target, the spring can move the diaphragm 502 and close the contacts 520. In other example embodiments, the agitator 114 may be clamped or otherwise coupled to a tube or dressing interface between the dressing 102 and the negative-pressure source 104. In some embodiments, the agitator 114 may have a tee fitting or micro-needle to puncture tubing, for example.

In some embodiments, such as the example of FIG. 5, the switch 204 may be normally closed. If the switch 204 is normally closed, the control circuit 800 may run the vibration motor 202 until the negative pressure in the first chamber 504 exceeds a threshold, opening the switch 204. Running the vibration motor 202 during pressure reduction may improve exudate flow. The threshold may correspond to a prescribed therapy pressure in some embodiments, but may also be greater or less than a prescribed therapy pressure. For example, the agitator 114 may vibrate on a low duty-cycle until negative-pressure in the first chamber 504 meets or exceeds a prescribed negative-pressure. In other embodiments, such as the example of FIG. 7, the agitator 114 may be configured with normally-open contacts, and may vibrate only if the negative-pressure in the first chamber 504 meets or exceeds a threshold pressure, such as a prescribed negative-pressure. Normally-open contacts may be advantageous, for example, to maximize battery life.

The systems, apparatuses, and methods described herein may provide significant advantages for managing fluid. For example, the agitator 114 can generate low amplitude vibrations, which can be transmitted through distribution components such as plastic tubing or dressing components.

These oscillations can direct kinetic energy into exudate to reduce or minimize the size of solids and lower the viscosity of the exudate. Lowering viscosity of exudate can reduce the frequency of blockages, particularly in tubes, which can be particularly useful for removing and managing fluid where blockages can occur. Vibrations may also micro-agitate the wound bed to encourage blood flow and granulation, and in some applications may also be useful for removing air from a fluid conductor.

While shown in a few illustrative embodiments, a person having ordinary skill in the art will recognize that the systems, apparatuses, and methods described herein are susceptible to various changes and modifications. Moreover, descriptions of various alternatives using terms such as "or" do not require mutual exclusivity unless clearly required by the context, and the indefinite articles "a" or "an" do not limit the subject to a single instance unless clearly required by the context. Components may be also be combined or eliminated in various configurations for purposes of sale, manufacture, assembly, or use. For example, in some configurations the dressing 102, the container 112, or both may be eliminated or separated from other components for manufacture or sale. In other example configurations, the controller 110 may also be manufactured, configured, assembled, or sold independently of other components.

The appended claims set forth novel and inventive aspects of the subject matter described above, but the claims may also encompass additional subject matter not specifically recited in detail. For example, certain features, elements, or aspects may be omitted from the claims if not necessary to distinguish the novel and inventive features from what is already known to a person having ordinary skill in the art. Features, elements, and aspects described herein may also be combined or replaced by alternative features serving the same, equivalent, or similar purpose without departing from the scope of the invention defined by the appended claims.

What is claimed is:

1. An apparatus for negative-pressure therapy, the apparatus comprising:
    a negative-pressure source;
    a distribution component configured to be fluidly coupled to the negative-pressure source; and
    an agitator configured to be coupled to the distribution component, the agitator comprising:
        an electrical energy source;
        a vibration motor configured to be coupled to the distribution component; and
        a pressure switch having an input aperture configured to be fluidly coupled to the negative-pressure source, and configured to electrically couple the vibration motor to the electrical energy source based on a pressure in the input aperture;
    wherein the agitator is operable to generate vibrations in the distribution component.

2. The apparatus of claim 1, wherein the pressure switch comprises:
    a first electrical contact coupled to the electrical energy source;
    a second electrical contact coupled to the vibration motor; and
    a piston configured to open and close the first electrical contact and the second electrical contact based on a pressure in the input aperture.

3. The apparatus of claim 1, wherein the distribution component is a dressing.

4. The apparatus of claim 1, further comprising a dressing, and wherein the agitator is coupled to the distribution component between the dressing and the negative-pressure source.

5. The apparatus of claim 1, wherein the distribution component is a tube fluidly coupled to the negative-pressure source.

6. The apparatus of claim 1, wherein the agitator further comprises a housing configured to enclose one or more of the electrical energy source, the vibration motor, and the pressure source.

7. A method of managing fluid in a negative-pressure therapy apparatus, the method comprising:
    delivering negative pressure to a distribution component; and
    agitating the distribution component with an agitator, the agitator comprising:
        an electrical energy source;
        a vibration motor configured to be coupled to the distribution component; and
        a pressure switch having an input aperture configured to be fluidly coupled to a negative-pressure source, and configured to electrically couple the vibration motor to the electrical energy source based on a pressure in the input aperture.

8. The method of claim 7, wherein agitating the distribution component comprises agitating the distribution component when the negative pressure is delivered to the distribution component.

9. The method of claim 7, wherein agitating the distribution component includes selectively providing vibration when the negative pressure is delivered.

10. The method of claim 9, wherein selectively providing the vibration includes turning the vibration motor on and off when the negative pressure is delivered.

11. The method of claim 9, wherein selectively providing the vibration includes turning a vibration motor on for a first predetermined period and turning the vibration motor off for a second predetermined period.

12. A method of treating a tissue site with negative pressure, the method comprising:
    applying a dressing to the tissue site;
    fluidly coupling the dressing to a negative-pressure source through a fluid conductor;
    coupling an agitator to the dressing or to the fluid conductor, the agitator comprising:
        an electrical energy source;
        a vibration motor; and
        a pressure switch having an input aperture configured to be fluidly coupled to the negative-pressure source, and configured to electrically couple the vibration motor to the electrical energy source based on a pressure in the input aperture;
    delivering negative pressure from the negative-pressure source to the dressing through the fluid conductor; and
    activating the agitator to generate vibrations.

13. The method of claim 12, wherein coupling the agitator to the dressing or the fluid conductor comprises coupling the vibration motor to the dressing or to the fluid conductor.

14. The method of claim 13, wherein the method further comprises fluidly coupling the pressure switch to the dressing or to the fluid conductor.

* * * * *